United States Patent [19]

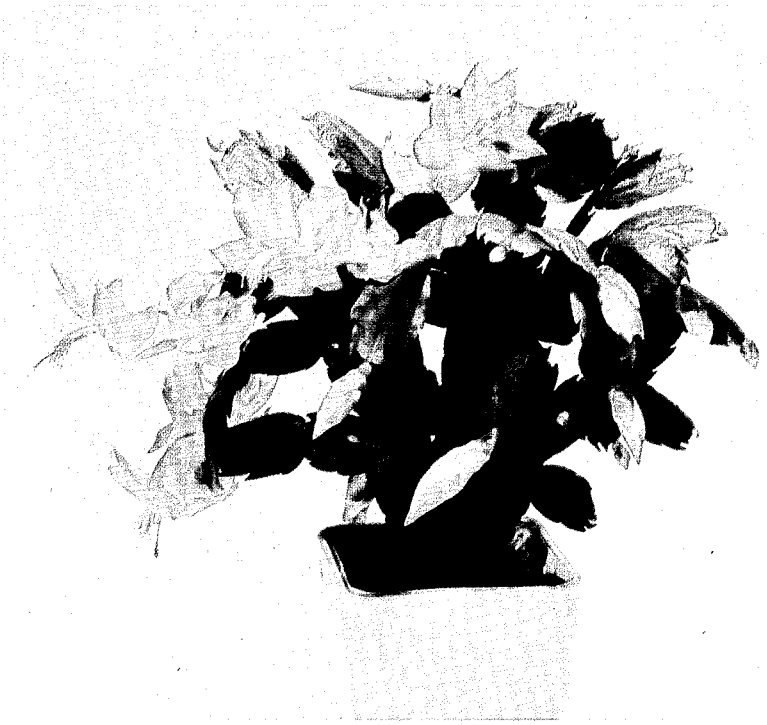
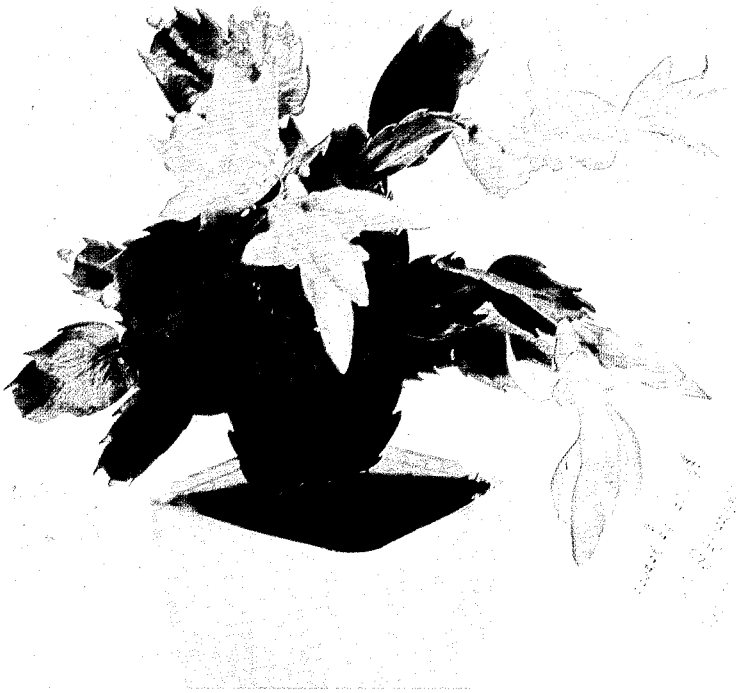

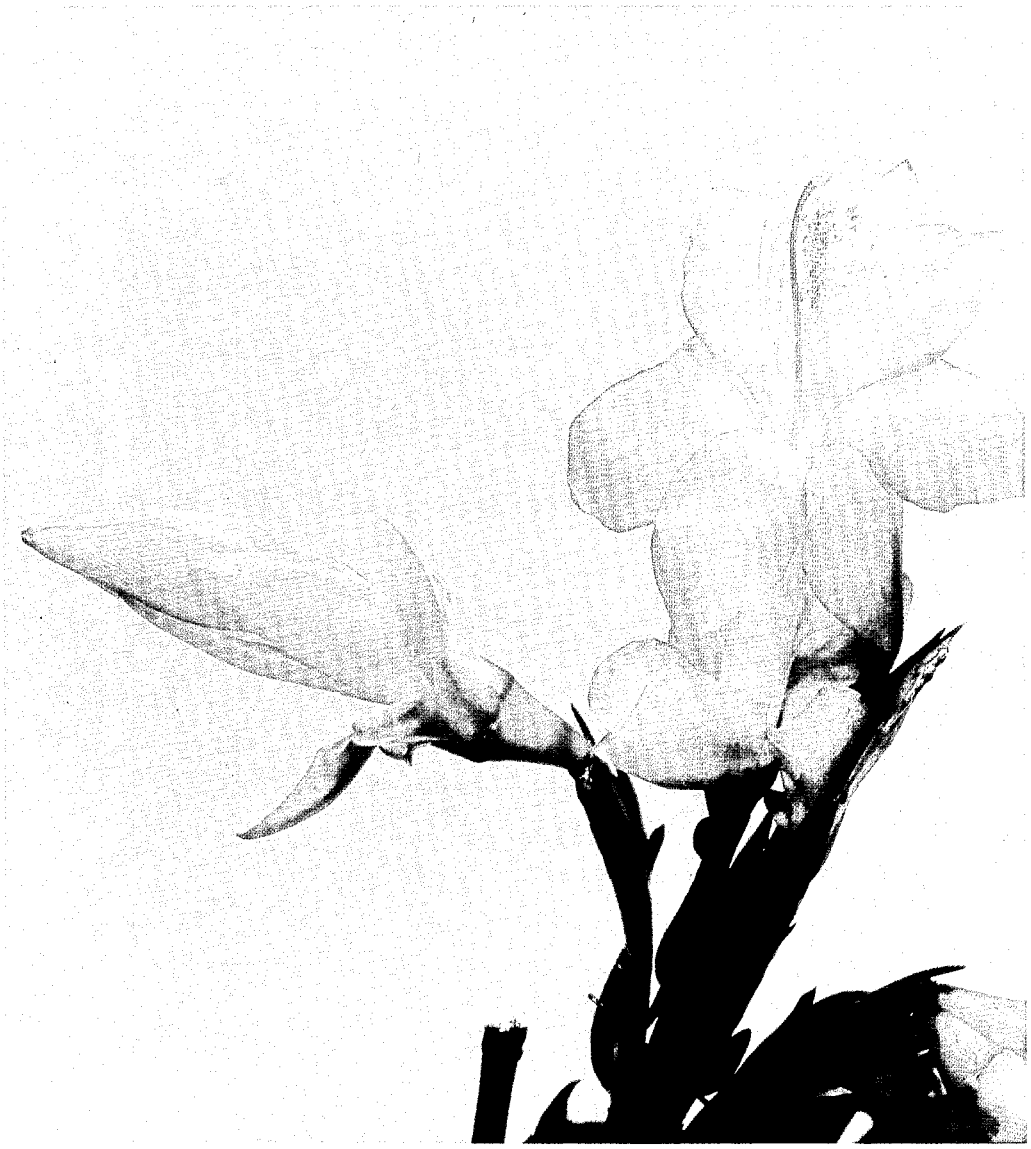

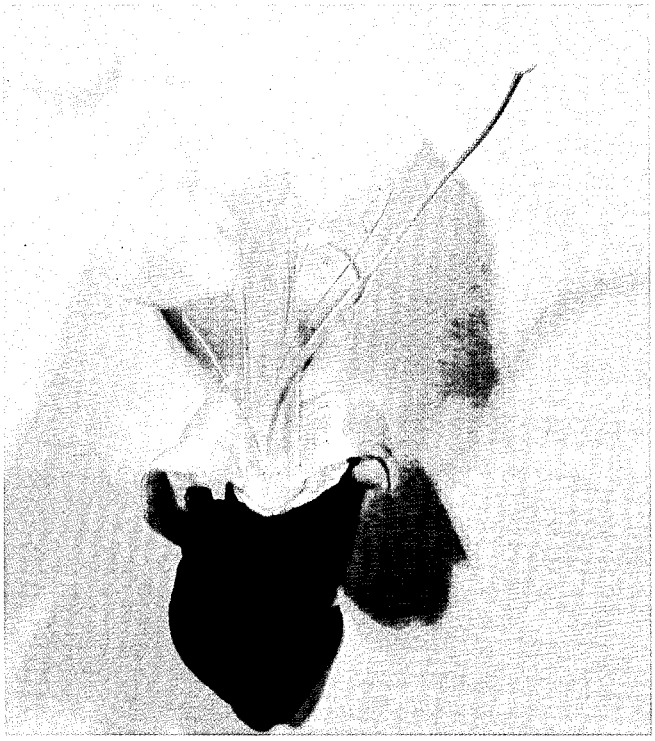
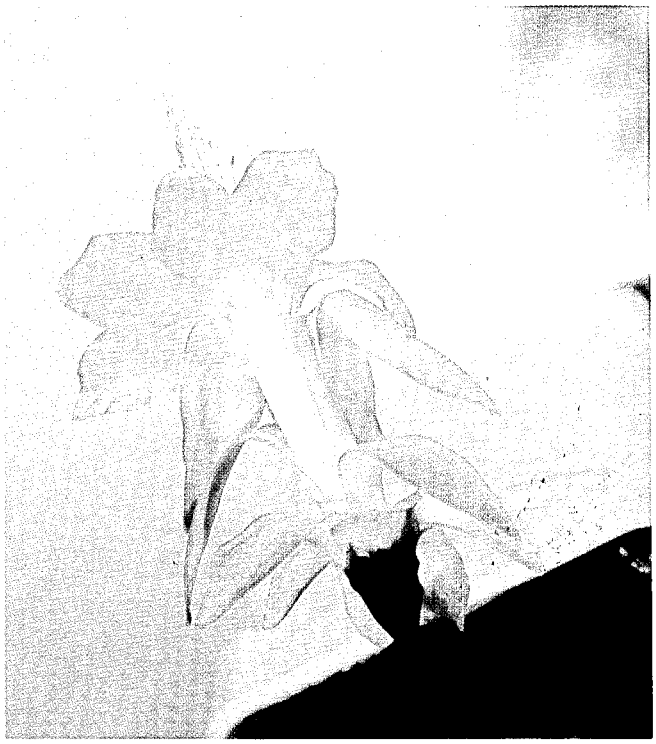

Cobia et al.

[11] Plant 4,197

[45] Jan. 24, 1978

[54] CACTACEAE PLANT

[75] Inventors: Barnell L. Cobia, Winter Garden; Stephen H. Griffith, Apopka, both of Fla.

[73] Assignee: B. L. Cobia, Inc., Winter Garden, Fla.

[21] Appl. No.: 760,337

[22] Filed: Jan. 18, 1977

[51] Int. Cl.[2] ..... A01H 5/00

[52] U.S. Cl. ..... Plt./88

[58] Field of Search ..... Plt./88

*Primary Examiner*—Robert E. Bagwill

*Attorney, Agent, or Firm*—Roger L. Martin

[57] ABSTRACT

A new and distinct plant variety of the Cactaceae family provides specimens that combine an upright, compact growth habit with a faster growth rate and a greater natural tendency to branch and produce a larger number of phylloclades without inducement by pruning than the 'Lavender Doll' and 'Kris Kringle' varieties of the *truncatus* species. The new variety provides specimens with phylloclades which are usually smaller in width and length dimensions than those of the 'Lavender Doll' variety. The specimens of the new plant variety have a substantially greater resistance to flower bud abscission than exhibited by the 'Lavender Doll' and 'Kris Kringle' varieties and also have resistances to nutrient deficiencies and fungus type diseases that are comparable to such varieties. The bloom usually occurs later in the growing season than that of the 'Lavender Doll' variety and it has a life of from about 6 to about 9 days. The tube laminating and tube forming tepals are characterized by marginal blade areas that in color are dominated by reddish purple and purplish red hues which penetrate deeply into the center field areas of the blades to provide a magenta appearing bloom coloration. The perianth tube is characterized by randomly arranged streaks or striations which in color are dominated by purplish pink hues and the variety is characterized by a degenerate carina that appears as a generally superior extension at the throat of the perianth tube. The style of the new variety is also commonly longer than those of the 'Lavender Doll' and 'Kris Kringle' varieties.

3 Drawing Figures

The invention relates to a new and distinct plant variety of the Cactaceae family and which has been named the *Zygocactus truncatus* 'Christmas Magic' by the inventors.

Certain plant varieties of the Cactaceae family are well known in the foliage plant market and among these is the *Zygocactus truncatus* variety commonly known as the 'Christmas Cheer' variety. This variety and its related varieties tend to bloom in the months of November and December in the Northern Hemisphere and hence their appearance in the retail market area is primarily during the Thanksgiving and Christmas seasons.

The 'Christmas Cheer' variety has what may be called a "salmon" color and among its descendants are the varieties of the *truncatus* species which have been named the 'Lavender Doll' and 'Kris Kringle'.

The 'Lavender Doll' variety has a generally "purplish" colored bloom and its characteristics are set forth in U.S. Plant Pat. No. 3,690. The 'Kris Kringle' variety, on the other hand, has a generally "reddish" colored bloom and its characteristics are generally set forth in U.S. Plant Pat. No. 3,688. Both of these patented varieties have a more upright, compact appearance than specimens of the 'Christmas Cheer' variety.

A general objective of the invention has been to develop a variety of the Cactaceae family which preserves or improves upon the upright, compact growth habits of the 'Lavender Doll' and 'Kris Kringle' varieties but which has a bloom color that is distinguishable from these varieties. Yet another objective of the invention has been to develop a variety which exhibits greater resistance to flower bud abscission than exhibited by the above named patented varieties.

The objectives of the invention have been fully realized by the development of the new plant variety hereinafter described in detail. The new plant variety was developed in a nursery located at Winter Garden, Fla., as a hybrid secured by cross pollinating the flower of a plant specimen of a variety developed by the inventors from a vegetative mutation that appeared on a specimen of the 'Lavender Doll' variety with pollen from a plant specimen of the 'Kris Kringle' variety. The seeds taken from the fertilized seed pod were cultivated at the mentioned nursery location and after prolonged observation of the seedlings, the hybridized plant of the new plant variety was selected and asexually reproduced by the inventors at the Winter Garden nursery by the propagation of stem cuttings taken from the original hybrid plant. The maternal plant variety is a research variety that has not appeared on the market. The variety generally resembles the 'Lavender Doll' variety except that it has slightly larger phylloclades and flower blooms and it exhibits poorer natural tendencies to branch without inducement by pruning during a growth period prior to blooming so that it has a less compact appearance in comparison to the 'Lavender Doll' variety.

Through successive propagations, it has been ascertained that specimens of the new plant variety generally resemble the parent varieties but are distinguishable from these varieties and from other related varieties known to the inventors by a growth habit which is evident in plant specimens propagated and grown under nursery conditions utilized in the growing of tropical plants at Winter Garden, Fla., as combining the following principal characteristics:

1. Upright, compact specimens that in comparison to the 'Lavender Doll' and 'Kris Kringle' varieties have a faster growth rate with a greater natural tendency to branch and produce a larger number of phylloclades without inducement by pruning during the growth period prior to initial blooming, 2. Phylloclades with commonly smaller width and length dimensions than those of the 'Lavender Doll' variety, 3. A substantially greater resistance to flower bud abscission than the 'Lavender Doll' and 'Kris Kringle' varieties and resistances to nutrient deficiencies and fungus type diseases that are comparable to the 'Kris Kringle' and 'Lavender Doll' varieties, 4. A generally "magenta" bloom coloration, with the bloom having a. an occurrence that is commonly from about 1 week to about 3 weeks later than that of comparably grown specimens of the 'Lavender Doll' variety, b. a bloom life of from about 6 to about 9 days, c. tube laminating and tube forming tepals with marginal blade areas that in color are dominated by reddish purple and/or purplish red hues which deeply penetrate into the center field areas of the blades, d. a perianth tube with a basic field that is translucent white and having randomly arranged longitudinally extending streaks or striations that in color are dominated by purplish pink hues, e. a carina which is degenerated at the throat of the perianth tube to a generally superior extension thereof, and f. a style that is commonly longer than those of the 'Lavender Doll' and 'Kris Kringle' varieties.

The accompanying drawings serve by color photographic means to illustrate the new plant variety and wherein the upper photograph on one sheet illustrates an 11 month old plant specimen that was propagated in January and pruned to one tier above the propagated stem cutting in June, while the lower photograph on the sheet shows a 6 month old plant specimen that was propagated in June and permitted to branch without inducement by pruning. A second sheet contains a close-up photograph of a bloom and the third sheet contains photographs further illustrating the bloom and bloom parts.

The following is a detailed descripton of the new plant variety with colors and hues, unless otherwise clearly indicated by the text through the absence of color notations being named in accord with the ISCC-NBS Method of Designating Colors, (U.S. Department of Commerce, National Bureau of Standards, Circular 553, issued No. 1, 1955) the named colors being interpreted from color notations derived by comparison with the color specimens in the current "Neighboring Hues Edition" of the Munsell Book of Color, published by the Munsell Color Company, Inc., of Baltimore, Md. The description is further based on observations of well fertilized plants of less than 1 year of age from initial propagation and which were grown under 50–75% shaded glasshouse nursery conditions in the Winter Garden, Fla., area and wherein temperatures range from 60°–85° F. during the winter months, from 75° to 95° F. during the summer months, and are ambient during the intervening periods.

DETAILED PLANT DESCRIPTION

Name: *Zygocactus truncatus* 'Christmas Magic'

Parentage:

*Maternal.*—Unnamed and unmarketed variety generally resembling the *Zygocactus truncatus* 'Lavender Doll' variety but with slightly larger phylloclades and blooms and with poorer natural branching characteristics than exhibited by the 'Lavender Doll' variety.

*Paternal.*—*Zygocactus truncatus* 'Kris Kringle'.

Classification:

*Botanic* (*Britton and Rose, the Cactaceae, Constable and Co., Ltd., London* 1937, *Vol IV*).—

| | |
|---|---|
| (1) Family: | *Cactaceae* |
| (2) Tribe: | *Cereeae* |
| (3) Sub-tribe: | *Epiphyllanae* |
| (4) Genus: | *Zygocactus* |
| (5) Species: | *truncatus* (Haworth) Schumann |

*Commercial.*—Thanksgiving-Christmas blooming cactus.

Form: Terrestrial, shade loving, succulent, leafless plant with jointed and branched stems.

Stems:

*General.*—Irregular with usually multichotomous branching of both upright and pendulous, adventitiously rootable, flattened phylloclades that have a prominent midrib and prominently toothed lateral wings.

*Phylloclades.*—General: Elongated and flat with transversely elongated, areole bearing, truncated apex, with inwardly tapering basal wing margins that merge through a broad usually pointed basal juncture with the phylloclade therebelow, and with an axillary areole associated with each tooth. Midrib: General — Extends longitudinally of phylloclade and continuously through joints with laterally tapering cortex at wing insertions. Pith surrounding vascular bundles that branch and provide lateral extensions of the bascular system to the marginal teeth. Texture — Smooth, waxy epidermis with wax in small embedded scales and becoming corky in basal stems areas with age. Size (2–6 mos. old) — Length: Usually between 35 and 53 mm. with the average for respective plant specimens being usually between 39 and 49 mm. Thickness: Usually between 2.4 and 6.7 mm. with the average for respective plant specimens being usually between 3.5 and 4.5 mm. Color (at maturity) — Commonly moderate yellow green (5 GY 5/6) (near 5 GY 5/4), moderate olive green (5 GY 4/4) (7.5 GY 4/4) (7.5 GY 3/4), grayish olive green (5 GY 4/2) and/or grayish green (10 GY 4/2). Wings: General shape — Generally flattened from midrib cortex to tooth insertions with slight thinning taper toward margins. Margins — Toothed (modified leaves). Texture — Succulent to leathery with smooth, waxy epidermis having wax arranged in small embedded scales and becoming corky in basal plant areas with age. Size (2–6 mos. old) — Center thickness: Usually between 1.4 and 3.0 mm. Width: (as measured from phylloclade axis to most offset lateral areole): Usually between 7 and 19 mm. Color (at maturity) — Commonly moderate yellow green (5 GY 5/6) (5 GY 5/4), moderate olive green (5 GY 4/4) (7.5 GY 4/4) (7.5 GY 3/4), grayish olive green (5 GY 4/2) and/or grayish green (10 GY 4/2). Teeth: General shape — Generally flattened and tapered along margins from wing insertions to an apex having a hyaline, single cell, pointed spine with nonpredictable bending. Adaxial marginal shape: Usually straight to slightly concave. Abaxial marginal shape: Generally convex. Orientation — Usually projects distally of phylloclade base in an alternate arrangement. Margins — Entire. Texture — Succulent to leathery with smooth, waxy epidermis having wax in small embedded scales and becoming corky in basal plant areas with age. Number — Usually from 6 to 8 per phylloclade. Size (2–6 mos. old) — Center thickness: Usually between 0.5 and 1.2 mm. Areole to apex dimension (adaxial marginal side): Usually between 2 and 8 mm. for teeth located distally of basal teeth. Color (at maturity) — Commonly moderate yellow green (near 5 GY 5/6) (near 5 GY 5/4), moderate olive green (5 GY 4/4) (7.5 GY 4/4) (7.5 GY 3/4), grayish olive green (5 GY 4/2) and/or grayish green (10 GY 4/2). Areoles: Terminal areole — Large, elongated, oval-shaped with several acicular bristles, copious multi-cellular hairs, and several buds that may mature into either new phylloclades or flowers. The opposite ends of the areole are located adjacent to subsidiary areoles which are in turn located at the axils of teeth that are located at the distal end of phylloclade. Axillary areoles — Acicular bristles without glochidia but having short, brownish to colorless, multi-cellular hairs. In areoles that are located below the teeth at the distal end of the phylloclade, there is usually only one bud that is frequently latent.

Buds: Unarmored, ovid and chlorophyllous at first emergence.

Flowers:

*General.*—Sessile, zygomorphic, usually solitary, terminal, perfect and epigynous with double hypanthium and tepals (undifferentiated whorled sepals and tepals) having a spiral emergence as a perianth provided with a sepaloid series of free tepals, a tube laminating series of tepals, and a tube forming series of united tepals.

*Sepaloid series.*—General: Free tepals inserted on top of ovary. Shape: Deltoid in outer members of the whorl and grading inwardly to tepals which are rhombic-like. All members have pointed tips and entire margins with sparse, irregular teeth appearing mainly in apex areas of the inner members of the whorl. Texture: Succulent and glabrous outer whorl members and grading inwardly in the whorl to silken blades with fleshy basal areas. Number: Usually 10 or 11. Size (at full bloom): Base-tip dimension — Usually less than 35 mm. Maximum width dimension — Usually less than 22 mm. Color: Varies from the outer members to the inner members with the smallest outer whorl tepal usually having a continuous field that in color is dominated by a yellow green hue. The inner whorl members have a translucent white basal area that extends distally in the tepal and merges with the color in the marginal blade area and which is dominated by a reddish purple hue. Commonly brilliant yellow green (near 5 GY 8/8), light yellow green (5 GY 8/6), strong yellow green (5 GY 7/8) (near 5 GY 6/8) (2.5 GY 7/8) and/or moderate yellow green (5 GY 7/6) (5 GY 6/6) in smallest outer whorl tepal members. Commonly strong reddish purple (10 P 5/10) (2.5 RP 5/10) (2.5 RP 4/10) and/or moderate reddish purple (10 P 5/8) (2.5 RP 5/8) (near 2.5 RP 5/6) in marginal blade areas of inner whorl members. Orientation at full bloom: Varying inwardly in the whorl from erect to recurve.

*Tube laminating series.*—General: Tepals inserted on ovary and basally united below the throat as outer laminations on the perianth tube and with progressively greater amounts of basal fusion inwardly in the whorl. Shape: Zygomorphic with rhombic, broadly oblanceolate, and broadly lanceolate blades having broad acute tips. Entire margins with sparse, irregular teeth mainly in apex areas. Texture: Glabrous with silken blades. Number: Usually 3. Size (at full bloom): Base-tip dimension — Usually between 35 and 59 mm. Maximum width dimension — Usually between 17 and 20 mm. Color: Tepals with translucent white basal areas and marginal blade areas which in color are dominated by purplish red and/or reddish purple hues that penetrate deeply into the center field areas for emergence with the distally extending basal area colorations. Commonly dark purplish red (5 RP 3/8), strong reddish purple (2.5 RP 4/10) and/or deep reddish purple (2.5 RP 3/10) in marginal blade areas. Orientation at full bloom: Perpendicular to recurve.

*Tube forming series.*—General: Tepals basally united to form hollow perianth tube that is inserted on ovary and equipped at its throat with a carina that is degenerated to a generally superior extension of the perianth tube. Shape: Perianth tube — Elongated and ellipsoidal in cross section with major ellipsoidal axis arranged at generally an acute angle with relation to the general plane of the supporting phylloclade. Blades — Nearly zygomorphic varying from lanceolate to elliptic with acute tips. Entire margins with sparse, irregular teeth mainly in apex areas. Carina (keel) — Degenerate and reduced to a slight superior extension of the perianth tube. Texture: Perianth tube — Thick, succulent and slightly ribbed. Blades — Translucent and silken. Blade Number: Usually 8 or 9. Size (at full bloom): Perianth tube — Base to keel length: Usually between 31 and 37 mm. along axis of tube with average length differences between measurements along dorsal and ventral side for respective specimens being usually between 1.5 and 6 mm. Internal Major axis (at throat): Usually between 8 and 12 mm. when measured perpendicular to axis of perianth tube. Internal minor axis (at throat): Usually between 5.5 and 11 mm. when measured perpendicular to axis of perianth tube. Blades — Length (keel to tip): Usually between 30 and 39 mm. Width (maximum): Usually between 13 and 20 mm. Color (at full bloom): Perianth tube — A basic field that is translucent white and having longitudinally extending, randomly arranged striations or streaks that in color are dominated by purple and/or purplish pink hues. Striations are commonly very pale purple (7.5 P 8/4), light purple (7.5 P 7/8) (7/5 P 7/6), moderate purplish pink (10 P 7/8) (10 P 7/6) (2.5 RP 7/6) (near 5 RP 7/6) and/or grayish purplish pink (near 10 P 7/4) (near 2.5 RP 7/4). Blades — A basal area which in color is dominated by purplish pink hues and a marginal blade area that in color is dominated by a reddish purple hue that penetrates deeply into the center field of the blade before emerging with the basal area coloration. Commonly pale purplish pink (near 10 P 8/4) and/or moderate purplish pink (10 P 7/8) (10 P 7/6) (near 2.5 RP 7/6) in the basal area. Commonly deep reddish purple (near 10 P 3/10), strong reddish purple (2.5 RP 4/10), moderate reddish purple (near 2.5 RP 4/8) and/or deep reddish purple (2.5 RP 3/10) (near 2.5 RP 3/8) in marginal blade areas. Carina (keel) — Translucent white. Orientation at full bloom: Acute to recurved.

*Androecium* (*stamens*).—General: Numerous exserted and diadelphous stamens with one group having filaments basally fused to the perianth tube and the other group having filaments basally united to form a nectary housing, thin annulus around the style. A deflexed, irregularly toothed margin or ruffle normally occurring at the throat of the annulus in antecedent varieties is either totally lacking or appears in a degenerate form in the instant variety. Stamen number: Tube attached group — Usually between 90 and 110. Basally united group — Usually between 17 and 22. Filaments: General — Translucent and glabrous with anther connective. Shape — Long, slender, terrete. Texture — Glabrous and silken. Color — Translucent white in basal area and in color dominated by a purplish pink hue in the distal area with the basal and distal area colors merging generally intermediate the proximal and distal ends. Commonly pale purplish pink (near 10 P 8/4) (2.5 RP 8/4) (5 RP 8/4), light purplish pink (5 RP 8/6), moderate purplish pink (10 P 7/8) (10 P 7/6) (5 RP 7/6) (7.5 RP 7/6) and/or grayish purplish pink (10 P 7/4) (near 2.5 RP 7/4) in distal area. Size (at full bloom) — Length: Tube attached group — Usually between 48 and 63 mm. Basally united group — Usually between 46 and 58 mm. Diameter: Usually between 0.2 and 0.3 mm. intermediate the opposite ends. Anthers: General — Adnate with four longitudinally dehiscent pollen sacs. Shape — Elongated. Texture — Waxy. Color (prior to dehiscing) — Usually pale greenish yellow (10 Y 9/4) and/or (7.5 Y 9/4).

*Gynoecium* (*pistil*).—General: Compound, parietal placentation with united style surrounded by annular diffuse nectary at its insertion. Style: General — Stout and inserted at ovary. Shape — Elongated and terrate. Texture — Fleshy and glabrous with short inner glutinous hairs at distal end. Color — A translucent white in the basal area with distal ends being in color dominated by a reddish purple hue. Commonly strong reddish purple (near 2.5 RP 5/10) (near 2.5 RP 4/10) and/or moderate reddish purple (near 2.5 RP 4/8) at distal end. Size (at full bloom) — Length: Usually between 66 and 72 mm. Diameter: Usually between 0.7 and 1.0 mm. intermediate the opposite ends. Stigma: General — Exserted and erect with usually from 5 to 7 inner marginally adhering lobes. Shape — Elongated and tapering toward lobe tips and having relatively blunt apices. Texture — Fleshy and smooth with short glutinous hairs. Color — Commonly very pale purple (7.5 P 8/4), pale purplish pink (10 P 8/4) (near 2.5 RP 8/4), moderate purplish pink (2.5 RP 7/6) and/or grayish purplish pink (2.5 RP 7/4). Size (lobe length at full bloom) — Usually between 3.4 and 5.8 mm. Ovary: Generally — Epigynous with thin epidermis and distally located concavity and with a single cavity having usually 5 to 6 carpels with numerous ovules. Shape — Ribbed and terrete and generally broadening from insertion to floral end. Texture — Succulent and glabrous with thin outer epidermis. Color — Commonly strong yellow green (2.5 GY 7/8) (5 GY 7/8) (near 5 GY 6/8), moderate yellow green (5GY 7/6) (5GY 6/6), light yellow green (5 GY 8/6) and/or brilliant yellow green (near 5 GY 8/8). Size (at full bloom) — Length (insertion to concavity base):Usually between 9 and 13 mm. Major axis (distal end of concavity): Usually between 8 and 11 mm. Minor axis (distal end of concavity): Usually between 6 and 10 mm.

Growing characteristics: An upright and compact (dense) appearance evidenced by erect stems with heavy (frequent) branching. A fast growth rate productive of more phylloclades than the 'Lavender Doll' and 'Kris Kringle' varieties without inducement by prunning during the growth period preceding blooming and a resistance to bud abscission that is substantially greater than the 'Lavender Doll' and 'Kris Kringle' varieties. A resistance to fungus diseases and nutrient deficiencies that is comparable to those of the 'Lavender Doll' and 'Kris Kringle' varieties and a greater natural tendency to branch without inducement by pruning than the 'Lavender Doll' and 'Kris Kringle' varieties. A degenerate carina in a bloom appearingly magenta in coloration. A bloom which commonly occurs about 1 week to 3 weeks later in the blooming season than those of the 'Lavender Doll' variety grown under comparable conditions and having a bloom life from about 6 to about 9 days.

The following is a general description of a specimen of the new plant variety that was grown from the propagation of a single phylloclade in a nursery at Winter Garden, Fla.

Age of plant: 6 months from initial propagation.
Branches from propagated cutting: 2.
Total number of phylloclades grown from cutting: 16.
General:

| Branch No. | No. of Phylloclades | Max. Length | No. of Tips |
|---|---|---|---|
| 1 | 7 | 144 mm. | 4 |
| 2 | 9 | 176 mm. | 5 |

Midribs:

| Branch No. | Length (avg.) | Thickness (avg.) |
|---|---|---|
| 1 | 48 mm. | 3.8 mm. |
| 2 | 47 mm. | 4.0mm. |

Wings:

| Branch No. | Center Thickness (avg.) | Max. Width (avg.) |
|---|---|---|
| 1 | 1.8 mm. | 10.6 mm. |
| 2 | 1.8 mm. | 12.8 mm. |

Teeth:

| Branch No. | No./Phylloclades (avg.) | Center Thickness (avg.) | Areole to Apex Dimension (avg.) | Tooth Angle (avg.) |
|---|---|---|---|---|
| 1 | 7 | .78 mm. | 4.8 mm. | |
| 2 | 7 | 1.1 mm. | 4.1 mm. | |

Phylloclade color: Moderate yellow green (5 GY 5/4) and moderate olive green (7.5 GY 4/4) (7.5 GY 3/4).

The following is a general description of a flower of the new plant variety which was bloomed in December on a plant grown under shaded glasshouse nursery conditions in Winter Garden, Fla.

Number of buds and blooms: 11.
Bloom life: 7 days.
Sepaloid series of tepals:
*Number.*—10.
*Size (at full bloom).*—Maximum base-tip dimension: 35 mm. Minimum base-tip dimension: 4 mm. Maximum width dimension: 21 mm.
*Color.*—Moderate yellow green (5 GY 7/6) (5GY 6/6) in continuous field of smaller tepals. Strong reddish purple (10 P 5/10) in marginal areas of the inner members and a translucent white basal area extending into the tepal.
Tube laminating series:
*Number.*—3.
*Size (at full bloom).*—Maximum base-tip dimension: 58 mm. Minimum base-tip dimension: 37 mm. Maximum width dimension: 19 mm. Minimum width dimension: 18 mm.
*Color.*—Strong reddish purple (2.5 RP 4/10) in marginal blade areas and translucent white in basal areas.
Tube forming series of tepals:
*Number.*—8.
*Size (at full bloom).*—Perianth tube: Base to keel length — 33 mm. Interior Major axis (at throat) — 10 mm. Interior minor axis (at throat) — 8 mm. Blades: Maximum length (keel to tip) — 37 mm. Minimum length (keel to tip) — 32 mm. Maximum width — 18 mm. Minimum width — 15 mm.
*Color.*—Perianth tube: A major field of translucent white with random striations of light purple (7.5 P 7/8) (7.5 P 7/6). Blades: Moderate purplish pink basel areas (10 P 7/8) (10 P 7/6) and a distal and marginal blade area that in color is strong reddish purple (2.5 RP 4/10). Carina (keel): Carina absent.
Androecium:
*Stamen number.*—Tube attached group: 99. Basally united group: 18.
*Filaments.*—Color: Translucent white in proximal area and moderate purplish pink (10 P 7/8) (10 P 7/6) in distal portion. Size (at full bloom): Length — Tube attached group: 51 mm. (avg.). Basally united group: 53 mm. (avg.). Diameter — 0.25 mm. intermediate the opposite ends.
*Anthers.*—Color (before dehiscing): Pale greenish yellow (10 Y 9/4).
Gynoecium (pistil):
*Style.*—Color: Translucent white in proximal area and strong reddish purple (near 2.5 RP 4/10) in distal area. Size (at full bloom): Length — 71 mm. Diameter — About 0.8 mm. intermediate the opposite ends.
*Stigma.*—Color: Moderate purplish pink (2.5 RP 7/6). Size (lobe length): 3.6 mm. (avg.).
*Ovary.*—Color: Strong yellow green (5GY 7/8) (2.5GY 7/8). Size (at full bloom): Length (insertion to concavity base) — 12 mm. Major axis (distal end of concavity) — 9 mm. Minor axis (distal end of concavity) — 8.5 mm.

We claim:

1. The new and distinct plant variety of the Cactaceae family as described and illustrated and which has a growth habit providing specimens that combine the following principal distinguishing characteristics:
1. Upright, compact appearing specimens that in comparison to the 'Lavender Doll' and 'Kris Kringle' varieties have a faster growth rate with a greater natural tendency to branch and produce a larger number of phylloclades without inducement by pruning during the growth period prior to blooming,
2. Phylloclades with commonly smaller width and length dimensions than those of the 'Lavender Doll' variety,
3. A substantially greater resistance to flower bud abscission than the 'Lavender Doll' and 'Kris Kringle' varieties and resistances to nutrient deficiencies and fungus type diseases that are comparable to those of the 'Lavender Doll' and 'Kris Kringle' varieties, and
4. A bloom which commonly occurs from about 1 week to 3 weeks later than those of the 'Lavender Doll' variety and has
a. A bloom life of from about 6 to about 9 days,
b. tube laminating and tube forming tepals with marginal blade areas that in color are dominated by reddish purple and/or purplish red hues which penetrate deeply into the center field areas of the tepal blades,
c. A perianth tube with a basic field that is translucent white and provided with randomly arranged, longitudinally extending streaks that in color are dominated by purplish pink hues,
d. A carina which has degenerated to a generally superior extension of the perianth tube, and
e. A style that is generally longer than those of the 'Lavender Doll' and 'Kris Kringle' varieties.

* * * * *

UNITED STATES PATENT AND TRADEMARK OFFICE

CERTIFICATE OF CORRECTION

PATENT NO. : Plant No. 4,197

DATED : January 24, 1978

INVENTOR(S) : Barnell L. Cobia and Stephen H. Griffith

It is certified that error appears in the above-identified patent and that said Letters Patent are hereby corrected as shown below:

Col. 3, Line 65, before "Maternal" insert -- A. --; Col. 4, Line 3, before "Paternal" insert -- B. --; Line 5, before "Botanic" insert -- A. --; Line 14, before "Commercial" insert -- B. --; Line 19, before "General" insert -- A. --; Line 24, before "Phylloclades" insert -- B. --; Line 24, before "General" insert -- [1] --; Line 30, before "Midrib" insert -- [2] --; Line 30, before "General" insert -- (a) --; Line 35, before "Texture" insert -- (b) --; Line 38, before "Size" insert -- (c) --; Line 38, before "Length" insert -- (1) --; Line 41, before "Thickness" insert -- (2) --; Line 44, before "Color)" insert -- (d) --; Line 48, before "Wings" insert -- [3] --; Line 49, before "General shape" insert -- (a) --; Line 51, before "Margins" insert -- (b) --; Line 52, before "Texture" insert -- (c) --; Line 55, before "Size" insert -- (d) --; Line 56, before "Center thickness" insert -- (1) --; Line 57, before "Width" insert -- (2) --; Line 59, before "Color (at maturity)" insert -- (e) --; Line 63, before "Teeth" insert -- [4] --; Line 64, before "General shape" insert -- (a) --; Line 67, before "Adaxial marginal shape" insert -- (1) --; Line 68, before "Ab-" insert -- (2) --; Col. 5, Line 1, before "Orienta-" insert -- (b) --; Line 3, before "Margins" insert -- (c) --; Line 4, before "Texture" insert -- (d) --; Line 7, before "Number" insert -- (e) --; Line 8, before "Size" insert -- (f) --; Line 8, before "Cen-" insert -- (1) --; Line 10, before "Areole" insert -- (2) --; Line 12, before "Color" insert -- (g) --; Line 17, before "Areoles" insert -- [5] --; Line 17, before "Termal areole" insert -- (a) --; Line 24, before "Axil-" insert -- (b) --; Line 34, before "General" insert -- A. --; Line 41, before "Sepaloid series" insert -- B. --; Line 41, before "General" insert -- [1] --; Line 42, before "Shape" insert -- [2] --; Line 47, before "Texture" insert -- [3] --; Line 50, before "Number" insert -- [4] --; Line 50, before "Size" insert -- [5] --; Line 51, before "Base-tip dimension" insert -- (a) --; Line 52, before "Maximum" insert -- (b) --; Line 53, before "Color" insert -- [6] --; Col. 6, Line 2, before "Orientation" insert -- [7] --; Line 4, before "Tube laminating series" insert -- C. --;

UNITED STATES PATENT AND TRADEMARK OFFICE

CERTIFICATE OF CORRECTION

PATENT NO. : Plant No. 4,197

DATED : January 24, 1978

INVENTOR(S) : Barnell L. Cobia and Stephen H. Griffith

It is certified that error appears in the above-identified patent and that said Letters Patent are hereby corrected as shown below:

Line 4, before "General" insert -- [1] --; Line 8, before "Shape" insert -- [2] --; Line 12, before "Texture" insert -- [3] --; Line 13, before "Number" insert -- [4] --; Line 13, before "Size" insert -- [5] --; Line 13, before "Base-tip" insert -- (a) --; Line 15, before "Maximum" insert -- (b) --; Line 16, before "Color" insert -- [6] --; Line 25, before "Orientation" insert -- [7] --; Line 27, before "Tube forming series" insert -- D. --; Line 27, before "General" insert -- [1] --; Line 31, before "Shape" insert -- [2] --; Line 31, before "Perianth" insert -- (a) --; Line 35, before "Blades" insert -- (b) --; Line 38, before "Carina (keel)" insert -- (c) --; Line 40, before "Texture" insert -- [3] --; Line 40, before "Perianth" insert -- (a) --; Line 42, before "Blades" insert -- (b) --; Line 42, before "Blade Number" insert -- [4] --; Line 43, before "Size" insert -- [5] --; Line 43, before "Perianth tube" insert -- (a) --; Line 44, before "Base to keel length" insert -- (1) --; Line 48, before "Internal Major" insert -- (2) --; Line 51 before "Internal minor axis" insert -- (3) --; Line 53, before "Blades" insert -- (b) --; Line 53, before "Length" insert -- (1) --; Line 55, before "Width" insert -- (2) --; Line 56, before "Color" insert -- [6] --; Line 56, before "Perianth tube" insert -- (a) --; Line 65, before "Blades" insert -- (b) --; Col. 7, Line 10, before "Carina (keel)" insert -- (c) --; Line 11, before "Orientation" insert -- [7] --; Line 13, before "Androecium" insert -- E. --; Line 13, before "General" insert -- [1] --; Line 22, before "Stamen number" insert -- [2] --; Line 23, before "Tube attached group" insert -- (a) --; Line 24, before "Basally united group" insert -- (b) --; Line 25, before "Filaments" insert -- [3] --; Line 25, before "General" insert -- (a) --; Line 26, before "Shape" insert -- (b) --; Line 27, before "Texture" insert -- (c) --; Line 28, before "Color" insert -- (d) --; Line 37, before "Size (at full bloom)" insert -- (e) --; Line 38, before "Length" insert -- (1) --; Line 38, before "Tube attached group" insert -- (a) --; Line 39, before "Basally united group" insert -- (b) --; Line 40, before "Diameter" insert -- (2) --; Line 42, before "Anthers" insert --

UNITED STATES PATENT AND TRADEMARK OFFICE

CERTIFICATE OF CORRECTION

PATENT NO. : Plant No. 4,197

DATED : January 24, 1978

INVENTOR(S) : Barnell L. Cobia and Stephen H. Griffith

It is certified that error appears in the above-identified patent and that said Letters Patent are hereby corrected as shown below:

[4] --; Line 42, before "General" insert -- (a) --; Line 43, before "Shape" insert -- (b) --; Line 44, before "Texture" insert -- (c) --; Line 44, before "Color" insert -- (d) --; Line 47, before "Gynoecium" insert -- F. --; Line 47, before "General" insert -- [1] --; Line 49, before "Style" insert -- [2] --; Line 50, before "General" insert -- (a) --; Line 50, before "Shape" insert -- (b) --; Line 51, before "Texture" insert -- (c) --; Line 53, before "Color" insert -- (d) --; Line 58, before "Size (at full bloom)" insert -- (e) --; Line 58, before "Length" insert -- (1) --; Line 59, before "Diameter" insert -- (2) --; Line 61, before "Stigma" insert -- [3] --; Line 61, before "General" insert -- (a) --; Line 63, before "Shape" insert -- (b) --; Line 65, before "Texture" insert -- (c) --; Line 66, before "Color" insert -- (d) --; Col. 8, Line 2, before "Size" insert -- (e) --; Line 3, before "Ovary" insert -- [4] --; Line 3, before "Generally" insert -- (a) --; Line 7, before "Shape" insert -- (b) --; Line 8, before "Texture" insert -- (c) --; Line 10 before "Color" insert -- (d) --; Line 14, before "Size" insert -- (e) --; Line 15, before "Length" insert -- (1) --; Line 16, before "Major axis" insert -- (2) --; Line 18, before "Minor axis" insert -- (3) --; Col. 9, Line 21, before "Number" insert -- (1) --; Line 22, before "Size" insert -- (2) --; Line 22, before "Maximum base-tip dimension" insert -- (a) --; Line 23, before "Minimum base-tip dimension" insert -- (b) --; Line 24, before "Maximum width dimension" insert -- (c) --; Line 25, before "Color" insert -- (3) --; Line 31, before "Number" insert -- (1) --; Line 32, before "Size" insert -- (2) --; Line 32, before "Maximum base-tip dimension" insert -- (a) --; Line 33, before "Minimum base-tip dimension" insert -- (b) --; Line 34, before "Maximum width dimension" insert -- (c) --; Line 34, before "Minimum" insert -- (d) --; Line 36, before "Color" insert -- (3) --; Line 40, before "Number" insert -- (1) --; Line 41, before "Size" insert -- (2) --; Line 41 before "Perianth tube" insert -- (a) --; Line 41, before "Base to keel" insert -- (1) --; Line 42, before "Interior Major axis" insert -- (2) --; Line 43, before "Interior Minor axis" insert --

UNITED STATES PATENT AND TRADEMARK OFFICE

CERTIFICATE OF CORRECTION

PATENT NO. : Plant No. 4,197

DATED : January 24, 1978

INVENTOR(S) : Barnell L. Cobia and Stephen H. Griffith

It is certified that error appears in the above-identified patent and that said Letters Patent are hereby corrected as shown below:

(3) --; Line 44, before "Blades" insert -- (b) --; Line 44, before "Maximum length" insert -- (1) --; Line 45, before "Minimum length" insert -- (2) --; Line 46, before "Maximum width" insert -- (3) --; Line 46, before "Minimum width" insert -- (4) --; Line 48, before "Color" insert -- (3) --; Line 48, before "Perianth tube" insert -- (a) --; Line 50, before "Blades" insert -- (b) --; Line 53, before "Ca-" insert -- (c) --; Line 56, before "Stamen number" insert -- (1) --; Line 56, before "Tube attached group" insert -- (a) --; Line 56, before "Basally" insert -- (b) --; Line 58, before "Filaments" insert -- (2) --; Line 58, before "Color" insert -- (a) --; Col. 10, Line 1, before "Size" insert -- (b) --; Line 2, before "Length" insert -- (1) --; Line 2, before "Tube attached group" insert -- (a) --; Line 3, before "Basally united group" insert -- (b) --; Line 3, before "Diameter" insert -- (2) --; Line 5, before "Anthers" insert -- (3) --; Line 5, before "Color" insert -- (a) --; Line 8, before "Style" insert -- (1) --; Line 8, before "Color" insert -- (a) --; Line 10, before "Size" insert -- (b) --; Line 10, before "Length" insert -- (1) --; Line 11, before "Diameter" insert -- (2) --; Line 13, before "Stigma" insert -- (2) --; Line 13, before "Color" insert -- (a) --; Line 14, before "Size" insert -- (b) --; Line 15, before "Ovary" insert -- (3) --; Line 15, before "Color" insert -- (a) --; Line 16, before "Size" insert -- (b) --; Line 16, before "Length" insert -- (1) --; Line 17, before "Major

UNITED STATES PATENT AND TRADEMARK OFFICE

CERTIFICATE OF CORRECTION

PATENT NO. : Plant No. 4,197

DATED : January 24, 1978

INVENTOR(S) : Barnell L. Cobia and Stephen H. Griffith

It is certified that error appears in the above-identified patent and that said Letters Patent are hereby corrected as shown below:

axis" insert -- (2) --; Line 18, before "Minor axis" insert -- (3) --;

Signed and Sealed this

*Thirteenth* Day of *November 1979*

[SEAL]

*Attest:*

RUTH C. MASON
*Attesting Officer*

LUTRELLE F. PARKER
*Acting Commissioner of Patents and Trademarks*